United States Patent [19]

Kahn et al.

[11] Patent Number: 5,210,283
[45] Date of Patent: May 11, 1993

[54] SYNTHESIS OF TETRAHYDROFURAN POLYMERS USING CALCINED SILICA-ALUMINA OR BEACHING EARTH CATALYSTS

[75] Inventors: Andrew P. Kahn, Wayne; Robert G. Gastinger, West Chester; Gangfeng Cai, West Chester, all of Pa.

[73] Assignee: ARCO Chemical Technology, L.P., Wilmington, Del.

[21] Appl. No.: 884,677

[22] Filed: May 18, 1992

[51] Int. Cl.$^5$ ................................. C07C 41/38
[52] U.S. Cl. ....................... 560/240; 568/617; 264/60; 502/56; 502/81
[58] Field of Search ............... 568/617; 562/607, 583, 562/590, 587; 264/56, 60; 560/240; 502/56, 81

[56] References Cited

U.S. PATENT DOCUMENTS

| | | | |
|---|---|---|---|
| 3,433,829 | 3/1969 | Dörfelt | 260/496 |
| 3,478,109 | 11/1969 | McConnell | 568/617 X |
| 4,189,566 | 2/1980 | Mueller et al. | 528/408 |
| 4,228,272 | 10/1980 | Del Pesco | 528/413 |
| 4,230,892 | 10/1980 | Pruckmayr | 568/617 |
| 4,235,751 | 11/1980 | Del Pesco | 252/450 |
| 4,243,799 | 1/1981 | Mueller et al. | 528/409 |
| 4,303,782 | 12/1981 | McHale et al. | 528/416 |
| 4,329,445 | 5/1982 | Del Pesco | 528/416 |
| 4,363,924 | 12/1982 | Mueller et al. | 549/509 |
| 4,510,333 | 4/1985 | Pruckmayr | 568/617 |
| 4,564,671 | 1/1986 | Mueller | 528/416 |
| 4,670,519 | 6/1987 | Mueller | 525/342 |
| 4,728,722 | 3/1988 | Mueller | 528/413 |
| 4,762,951 | 8/1988 | Mueller | 568/617 |
| 4,803,299 | 2/1989 | Mueller | 560/240 |
| 4,933,503 | 6/1990 | Mueller | 568/621 |
| 5,053,553 | 10/1991 | Dorai | 568/617 |

FOREIGN PATENT DOCUMENTS 854958 11/1960 United Kingdom .

Primary Examiner—Arthur C. Prescott
Attorney, Agent, or Firm—Jonathan L. Schuchardt

[57] ABSTRACT

Tetrahydrofuran is polymerized in the presence of a carboxylic acid anhydride and a solid acid catalyst that has been calcined at a temperature greater than about 600° C. Calcined bleaching earth catalysts give THF polymer products having a narrow molecular weight distribution; calcining amorphous silica-aluminas improves their activity toward THF polymerization.

20 Claims, No Drawings

SYNTHESIS OF TETRAHYDROFURAN POLYMERS USING CALCINED SILICA-ALUMINA OR BEACHING EARTH CATALYSTS

FIELD OF THE INVENTION

The invention relates to the synthesis of tetrahydrofuran polymers (THF polymers) using solid acid catalysts, and more particularly, to a process for improving catalyst activity and/or product quality by calcining the catalysts at elevated temperatures (>600° C.). The polymers are especially valuable for the manufacture of polyurethanes and thermoplastic polyesters having superior properties.

BACKGROUND OF THE INVENTION

Solid acid catalysts, including acid-washed bleaching earths, can be used in combination with an activator (such as an epoxide or a carboxylic acid anhydride) to initiate the polymerization of tetrahydrofuran. See, for example, U.S. Pat. Nos. 3,433,829, 4,189,566, and 4,243,799. Bleaching earths known in the art include naturally occurring aluminum hydrosilicates and aluminum/magnesium hydrosilicates of the montmorillonite type. The clays are normally activated by acid washing. When a carboxylic acid anhydride is used as the activator, the resulting polytetramethylene ether polymer has ester end groups. The ester end groups can be converted to hydroxyl end groups by base-catalyzed transesterification with an alcohol (see U.S. Pat. No. 4,230,892) or by catalytic hydrogenation.

A key disadvantage of the bleaching earth catalysts is that the polymers produced have higher polydispersities ($M_w/M_n$) than desirable, typically 3-4 at molecular weights of about 400 to 3,000. It is well known in the art that the molecular weight distribution (MWD) of the THF polymer impacts the properties of the polyurethanes or polyesters made therefrom. In general, mechanical properties of finished products are superior when THF polymers having a relatively narrow molecular weight distribution are used (see U.S. Pat. No. 4,933,503, column 2).

There are two general approaches to obtaining THF polymers having a relatively narrow MWD. In one approach, a THF polymer having a broad MWD is prepared, and the product is post-treated either by distillation to separate low molecular weight oligomers, selective depolymerization (see, for example, U.S. Pat. No. 4,363,924), selective solvent extraction with water/alcohol/hydrocarbon systems (see U.S. Pat. No. 4,762,951), or a combination of these techniques (see U.S. Pat. No. 4,933,503). Post-polymerization techniques are typically expensive, labor-intensive, and time consuming. A second general strategy is aimed at eliminating the need for post-treatment by preparing THF polymers having a narrow MWD. In one method, a low concentration of an alkylene oxide is maintained throughout the THF polymerization (U.S. Pat. No. 4,728,722). In another method, the mole ratio of the reactants and the reaction temperature are carefully controlled (U.S. Pat. No. 4,510,333). Unfortunately, these approaches are complicated and not completely satisfactory.

Other than acid-washed bleaching earths and some sulfonic acid resins, solid acid catalysts useful for preparing THF polymers in the commercially important 250-3,000 molecular weight range are not generally known. Copending application Ser. No. 07/839,538, filed Feb. 19, 1992, discloses a new class of THF polymerization catalysts: amorphous silica-aluminas. The silica-aluminas give THF polymers with commercially useful molecular weight distributions. Unfortunately, however, these catalysts tend to lose activity under conditions of continuous operation. In addition, some silica-aluminas will not ordinarily catalyze THF polymerization.

SUMMARY OF THE INVENTION

An object of the present invention is to provide bleaching earth catalysts that inherently give THF polymers having a narrow molecular weight distribution. Preferably, the catalysts are effective, easily prepared, and can be used in a simple process to make narrow MWD polymers, thereby eliminating the need for costly post-polymerization treatments.

Another object of the invention is to provide amorphous silica-aluminas having a reduced tendency to deactivate during continuous use. Another object of the invention is to provide active THF polymerization catalysts from silica-aluminas that ordinarily have little or no activity toward THF polymerization.

The invention is a process for producing a tetrahydrofuran polymer. The process comprises polymerizing tetrahydrofuran in the presence of a carboxylic acid anhydride and an effective amount of a solid acid catalyst selected from the group consisting of acid-washed bleaching earths and amorphous silica-aluminas. A key feature of the invention is that the solid acid catalyst is calcined at a temperature greater than about 600° C. prior to use in the process.

We have now surprisingly found that acid-washed bleaching earths that have been calcined at temperatures greater than about 600° C. give THF polymer products having substantially narrowed molecular weight distributions.

We have also found that the activity of amorphous silica alumina catalysts toward THF polymerization improves as a result of calcining the amorphous silica-alumina at temperatures greater than about 600° C. prior to use. In addition, some amorphous silica-aluminas that have little or no apparent activity for THF polymerization can be activated by calcination at temperatures greater than about 600° C.

DETAILED DESCRIPTION OF THE INVENTION

In the process of the invention, a tetrahydrofuran polymer having a relatively narrow molecular weight distribution is produced by polymerizing THF and optionally other monomers in the presence of a carboxylic acid anhydride and a calcined solid acid catalyst selected from the group consisting of amorphous silica-alumina and acid-washed bleaching earths.

Any grade of tetrahydrofuran can be used in the process of the invention. Optionally, one or more additional cationically polymerizable monomers can also be included. Suitable copolymerizable monomers include epoxides such as ethylene oxide and propylene oxide, oxetanes, substituted oxolanes such as 3-methyltetrahydrofuran, and the like, and mixtures thereof. Preferred comonomers are ethylene oxide and propylene oxide.

A carboxylic acid anhydride is used as an activator. Suitable carboxylic acid anhydrides are anhydrides of aliphatic carboxylic acids of 2-12 carbon atoms and anhydrides of aromatic and aliphatic dicarboxylic acids. Suitable anhydrides include, but are not limited to, acetic, propionic, butyric, valeric, caproic, phthalic, maleic, succinic, and the like, and mixtures thereof. Acetic anhydride is preferred.

The amount of carboxylic acid anhydride is not critical, but the ratio of tetrahydrofuran to anhydride affects the molecular weight of the polymer obtained. Generally, it is preferred that the mole ratio of tetrahydrofuran to carboxylic acid anhydride be within the range of about 1 to about 50. A more preferred range is from about 10 to about 30. In general, the higher the mole ratio of tetrahydrofuran to anhydride, the higher the molecular weight of the resulting polymer.

Solid acid catalysts useful in the invention include amorphous silica-aluminas. These catalysts typically contain from about 10 to about 30 weight percent alumina and have surface areas within the range of about 20–500 m$^2$/g. Suitable catalysts are available from Davison/Grace (grades 970-13, 979, 980-13, 980-25, 135, MS13/110). Any form of the catalyst, e.g., powder, granule, pellet, etc., is suitable. These synthetic, amorphous materials can be prepared from hydrolyzable mixtures of silicon and aluminum compounds.

Catalysts useful in the invention also include bleaching earths or clays. Suitable bleaching earths include naturally occurring aluminum hydrosilicates and aluminum/magnesium hydrosilicates of the montmorillonite type. Synthetic bleaching earths, such as those described in British Patent No. 854,958, are also suitable. Suitable bleaching earths include kaolinites, bentonites, fuller's earths, and the like. "Tonsil" bleaching earths, which are available commercially from Sud-Chemie AG, "F-24" bleaching earth, a product of Englehard, and "KWK Volclay" bentonite, a product of American Colloid Company, are examples of suitable bleaching earths.

Bleaching earths are commercially available in non-acid washed and acid-washed forms. Commercially available acid-washed clays are suitable for use in the process of the invention without further acid washing.

The bleaching earths are normally activated by acid washing. Simply contacting the bleaching earth with a dilute solution of a mineral acid (hydrochloric, nitric, phosphoric, sulfuric) in any desired manner activates the bleaching earth. In one suitable method, the bleaching earth is stirred gently at room temperature with 5–10% hydrochloric acid for about an hour.

The bleaching earth is separated from the acid solution by any convenient method, including filtration, centrifugation, or decantation, and the catalyst is rinsed with water to remove residual acid.

It is conventional to then dry the bleaching earth under vacuum at 100° C. to 200° C. (see, for example, U.S. Pat. No. 4,253,751, column 2, line 15, and U.S. Pat. No. 4,189,566, column 5, lines 42–47). Higher temperatures can be used to dry the bleaching earth, but temperatures in the 100°–200° C. range are commonly used because essentially quantitative water removal can be achieved in the 100°–200° C. range. As shown in Examples 1–5 below, the weight loss from catalysts calcined at 200° C. is about the same as that observed from catalysts calcined at 600°–800° C.

A key feature of the invention is that the solid acid catalyst (amorphous silica-alumina or acid-washed bleaching earth) is calcined at a temperature greater than about 600° C. prior to use as a THF polymerization catalyst. Preferably, the solid acid catalyst is calcined at a temperature within the range of about 600° C. to about 1000° C. A more preferred range is from about 600° C. to about 800° C. Calcining the solid acid catalyst at elevated temperature does more than dry the catalyst—with silica-aluminas it also activates the catalyst, and with bleaching earths, it makes the preparation of narrow MWD polymers possible.

The calcination can be performed over any desired time period. Preferably, the catalyst is calcined at 600°–1000° C. for up to about 72 h, and more preferably, from about 0.1 to about 20 h. If desired, the catalyst can be brought up to 600° C. or greater, and then be immediately cooled to room temperature. Particularly at higher calcination temperatures, relatively brief calcination times may be desirable (compare Examples 11 and 12).

We have surprisingly found that acid-washed bleaching earths that have been calcined at a temperature greater than about 600° C. give THF polymer products having substantially narrowed molecular weight distributions. This discovery is truly valuable in view of how easily the process of the invention can be practiced and how difficult alternative processes are. Additional monomers need not be added, and control of reaction temperature is not especially critical, so the process of the invention is simpler than other approaches to producing THF polymers having an "inherently" narrow MWD. The high cost and complexity of known solvent extraction and distillation post-treatments for narrowing MWD is also avoided. Polydispersities ($M_w/M_n$) less than about 3 are typical for THF polymer products in the commercially useful 250–3,000 molecular weight range made by the process of the invention. Examples 1–4 and 8–12 (below) illustrate the effect of calcination at temperatures within the 600°–800° C. range on molecular weight distribution with bleaching earth catalysts.

We have also found that calcination at temperatures greater than about 600° C. unexpectedly improves the activity of amorphous silica-aluminas. These catalysts were previously found (see application Ser. No. 07/839,538) to give THF polymers with inherently narrow molecular weight distributions. Silica-aluminas that are normally active can be made more productive by calcination. For example, an untreated amorphous silica-alumina catalyst (Davison/Grace grade 979) deactivates during continuous operation, with the yield of polymer decreasing from 58% to 30% after 15 days of continuous use. When the same grade of silica-alumina is calcined at 600° C. prior to use, the catalyst maintains high activity: the yield of polymer is 40% after 38 days of continuous use. Interestingly, some amorphous silica-aluminas that have little or no apparent activity for THF polymerization can be activated by calcination at temperatures greater than about 600° C. (see Examples 6–7, below).

The THF polymers from the process of the invention have molecular weights that make them useful intermediates for polyurethane applications. Typically, the number average molecular weights ($M_n$) obtained will be within the range of about 200 to about 5,000, preferably from about 250 to about 3,000.

The process of the invention can be performed at any desired temperature. Especially suitable is a temperature range from about 20° C. to about 70° C. A more preferred range is from about 40° C. to about 60° C.

The process of the invention can be performed at pressures less than, greater than, or equal to atmospheric pressure, although it is typically most convenient to perform the process at atmospheric pressure.

The process of the invention can be performed batchwise, semi-batchwise, or continuously, as desired. A continuous process is preferred.

An inert organic solvent can be employed if desired. Suitable organic solvents include, but are not limited to, aliphatic and aromatic hydrocarbons, halogenated hydrocarbons, esters, ketones, glycol ether esters, and the like. Any solvent that is stable to the reaction conditions, will not react with the carboxylic acid anhydride, and will dissolve the reactants and the polymer products is suitable.

The products usually isolated from the process of the invention are ester-terminated polyethers. These materials are usually less useful than the hydroxy-terminated polymers. The ester groups can be removed by any conventional method known to those skilled in the art, including base-catalyzed transesterification (see U.S. Pat. No. 4,230,892) or catalytic hydrogenation. Molecular weight distribution remains fairly constant during this step, as shown in the examples.

The following examples merely illustrate the invention. Those skilled in the art will recognize numerous variations that are within the spirit of the invention and scope of the claims.

EXAMPLES 1-4

Preparation of Polytetramethylene Ether Glycols Using Calcined Bleaching Earths Continuous Process

EXAMPLE 1

Calcination at 600° C.

"F-24" bleaching earth (product of Englehard) is calcined at 600° C. in air for 10 h. The weight loss of volatile material from the catalyst as a result of calcination is 20.7%. A jacketed reactor tube (2.5 cm diameter) is wet packed in tetrahydrofuran with the bleaching earth to give a 24-cm long catalyst bed. The reactor is heated to 50° C. A feed mixture containing tetrahydrofuran/acetic anhydride (15:1 molar ratio) is passed upwardly through the bed at a rate of 2.5 mL/min. A colorless solution is collected, from which polytetramethylene ether glycol diacetate ($M_n=970$ g/mol, $M_w/M_n=3.0$) is obtained (53% yield based on tetrahydrofuran) by distilling off the unreacted feed. Transesterification of this material by the method disclosed in U.S. Pat. No. 4,230,892 provides polytetramethylene ether glycol having $M_n=870$ g/mol, and $M_w/M_n=3.0$.

EXAMPLE 2

Calcination at 700° C.

The procedure of Example 1 is followed, except that the bleaching earth catalyst is calcined at 700° C. in air for 10 h prior to use. The weight loss of volatile material from the catalyst as a result of calcination is 21.6%. Polytetramethylene ether glycol diacetate ($M_n=830$ g/mol, $M_w/M_n=2.7$) is obtained in 54% yield based on tetrahydrofuran. Transesterification gives polytetramethylene ether glycol having $M_n=790$ g/mol and $M_w/M_n=2.7$.

EXAMPLE 3

Calcination at 750° C.

The procedure of Example 1 is followed, except that the bleaching earth catalyst is calcined at 750° C. in air for 10 h prior to use. The weight loss of volatile material from the catalyst as a result of calcination is 22.4%. Polytetramethylene ether glycol diacetate ($M_n=800$ g/mol, $M_w/M_n=2.4$) is obtained in 55% yield based on tetrahydrofuran. Transesterification gives polytetramethylene ether glycol having $M_n=750$ g/mol and $M_w/M_n=2.5$.

EXAMPLE 4

Calcination at 800° C.

The procedure of Example 1 is followed, except that the bleaching earth catalyst is calcined at 800° C. in air for 10 h prior to use. The weight loss of volatile material from the catalyst as a result of calcination is 23.1%. Polytetramethylene ether glycol diacetate ($M_n=1,300$ g/mol, $M_w/M_n=2.3$) is obtained in 41% yield. Transesterification gives polytetramethylene ether glycol having $M_n=1,200$ g/mol and $M_w/M_n=2.4$.

COMPARATIVE EXAMPLE 5

Preparation of Polytetramethylene Ether Glycols Using Bleaching Earth Catalysts Continuous Process Calcination at 200° C.

The procedure of Example 1 is followed, except that the bleaching earth catalyst is calcined in air at 200° C. for 10 hours prior to use. The weight loss of volatile material from the catalyst as a result of drying is 21.4%. Polytetramethylene ether glycol diacetate ($M_n=740$ g/mol, $M_w/M_n=3.4$) is obtained in 50% yield. Transesterification gives polytetramethylene ether glycol having $M_n=700$ g/mol and $M_w/M_n 3.5$.

EXAMPLES 6-7

Preparation of Polytetramethylene Ether Glycols Using Amorphous Silica-Alumina Batch Process

EXAMPLE 6

Calcination at 600° C.

A stirred reaction vessel is charged with tetrahydrofuran (432 g) and acetic anhydride (41 g). The mixture is heated to 50° C. Silica-alumina (45 g, Davison/Grace, grade 135) that has been calcined at 600° C. in air for 10 h is added. The weight loss of volatile material from the catalyst as a result of drying is 11.5%. After 3 h, the reaction mixture is filtered to remove the bleaching earth, and unreacted monomers are removed from the filtrate by distillation. The yield of polytetramethylene ether glycol diacetate is 48% based on tetrahydrofuran. Transesterification with methanol gives polytetramethylene ether glycol having $M_n=660$ and $M_w/M_n=1.9$.

COMPARATIVE EXAMPLE 7

Silica-Alumina Calcined at 120° C. or 200° C.

The procedure of Example 6 is followed, except that the amorphous silica-alumina is dried under vacuum at 120° C. for 72 hours, or is calcined in air at 200° C. for 10 h, prior to use. Weight loss from the catalysts as a result of calcination is 5.4% (120° C.) or 5.5% (200° C.). The yield of polytetramethylene ether glycol diacetate in both cases is less than 1%.

EXAMPLES 8-13

Preparation of Polytetramethylene Ether Glycols Using Acid-Washed Bleaching Earth Batch Process

EXAMPLE 8

Calcination at 600° C.

A stirred reaction vessel is charged with tetrahydrofuran (144 g) and acetic anhydride (13.6 g), and is heated to 50° C. "F-24" bleaching earth (30 g, product of Englehard) that has been calcined at 600° C. for 10 h prior to use is added to the mixture. After 3 h, the reaction mixture is filtered to remove the bleaching earth, and unreacted THF and acetic anhydride are removed by distillation. The yield of polytetramethylene ether glycol diacetate (based on THF) is 56%. The polymer has $M_n=760$ g/mol and $M_w/M_n=2.6$.

EXAMPLE 9

Calcination at 700° C.

The procedure of Example 8 is followed except that the bleaching earth is calcined at 700° C. for 10 h prior to use. Yield of diacetate: 51%. The polymer has $M_n=700$ g/mol and $M_w/M_n=2.2$.

EXAMPLE 10

Calcination at 750° C.

The procedure of Example 8 is followed except that the bleaching earth is calcined at 750° C. for 10 h prior to use. Yield of diacetate: 66%. The polymer has $M_n=780$ g/mol and $M_w/M_n=2.3$.

EXAMPLE 11

Calcination at 800° C. (10 hours)

The procedure of Example 8 is followed except that the bleaching earth is calcined at 800° C. for 10 h prior to use. Yield of diacetate: 44%. The polymer has $M_n=1,300$ g/mol and $M_w/M_n=2.1$.

EXAMPLE 12

Calcination at 800° C. (1 hour)

The procedure of Example 8 is followed except that the bleaching earth is calcined at 800° C. for 1 h prior to use. Yield of diacetate: 66%. The polymer has $M_n=770$ g/mol and $M_w/M_n=2.2$.

COMPARATIVE EXAMPLE 13

Calcination at 200° C.

The procedure of Example 8 is followed, except that the catalyst is calcined in air at 200° C. prior to use. The yield of diacetate is 51%. The polymer has $M_n=660$ g/mol and $M_w/M_n=3.0$.

The preceding examples are meant only as illustrations; the true metes and bounds of the invention are defined by the following claims.

We claim:

1. A process for producing a tetrahydrofuran polymer, said process comprising polymerizing tetrahydrofuran in the presence of a carboxylic acid anhydride and an effective amount of a solid acid catalyst selected from the group consisting of amorphous silica-aluminas and acid-washed bleaching earths, wherein the catalyst is calcined at a temperature greater than about 600° C. prior to use in the process.

2. The process of claim 1 wherein the carboxylic acid anhydride is acetic anhydride.

3. The process of claim 1 wherein the catalyst is calcined at a temperature within the range of about 600° C. to about 800° C.

4. The process of claim 1 wherein the resulting tetrahydrofuran polymer has a number average molecular weight within the range of about 200 to about 3,000, and a molecular weight distribution $(M_w/M_n)$ less than about 3.0.

5. The process of claim 1 wherein tetrahydrofuran is copolymerized with a cationically polymerizable monomer.

6. The process of claim 1 wherein the polymerization is performed at a temperature within the range of about 20° C. to about 70° C.

7. A process for producing a tetrahydrofuran polymer, said process comprising polymerizing tetrahydrofuran in the presence of a carboxylic acid anhydride and an effective amount of amorphous silica-alumina, wherein the silica-alumina is calcined at a temperature greater than about 600° C. prior to use in the process, and wherein the activity of the silica-alumina toward tetrahydrofuran polymerization improves as a result of calcination.

8. The process of claim 7 wherein the carboxylic acid anhydride is acetic anhydride.

9. The process of claim 7 wherein the silica-alumina is calcined at a temperature within the range of about 600° C. to about 800° C.

10. The process of claim 7 wherein the resulting tetrahydrofuran polymer has a number average molecular weight within the range of about 200 to about 3,000, and a molecular weight distribution $(M_w/M_n)$ less than about 3.0.

11. The process of claim 7 wherein tetrahydrofuran is copolymerized with a cationically polymerizable monomer.

12. The process of claim 7 wherein the polymerization is performed at a temperature within the range of about 20° C. to about 70° C.

13. A process for producing a tetrahydrofuran polymer, said process comprising polymerizing tetrahydrofuran in the presence of a carboxylic acid anhydride and an effective amount of an acid-washed bleaching earth, wherein the bleaching earth is calcined at a temperature greater than about 600° C. prior to use in the process, and wherein the molecular weight distribution of the tetrahydrofuran polymer is narrowed as a result of calcination.

14. The process of claim 13 wherein the carboxylic acid anhydride is acetic anhydride.

15. The process of claim 13 wherein the bleaching earth is calcined at a temperature within the range of about 600° C. to about 800° C.

16. The process of claim 13 wherein the resulting tetrahydrofuran polymer has a number average molecular weight within the range of about 200 to about 3,000, and a molecular weight distribution $(M_w/M_n)$ less than about 3.0.

17. The process of claim 13 wherein tetrahydrofuran is copolymerized with a cationically polymerizable monomer.

18. The process of claim 13 wherein the polymerization is performed at a temperature within the range of about 20° C. to about 70° C.

19. A method of preparing an improved tetrahydrofuran polymerization catalyst, said method comprising calcining a solid acid catalyst selected from the group consisting of acid-washed bleaching earths and amorphous silica-aluminas at a temperature greater than about 600° C.

20. The method of claim 19 wherein the catalyst is calcined at a temperature within the range of about 600° C. to about 800° C.

* * * * *